United States Patent
Kurihara et al.

(10) Patent No.: US 6,752,867 B1
(45) Date of Patent: Jun. 22, 2004

(54) ANTIBACTERIAL AGENT FOR CONCRETE, CONCRETE COMPOSITIONS AND CONCRETE PRODUCTS

(75) Inventors: Yasuo Kurihara, Nagoya (JP); Javier Takahashi, Nagoya (JP); Yuji Kamiike, Nagoya (JP)

(73) Assignee: Sinanen Zeomic Co., Ltd., Nagoya (JP)

( * ) Notice: Subject to any disclaimer, the term of this patent is extended or adjusted under 35 U.S.C. 154(b) by 0 days.

(21) Appl. No.: 10/338,662

(22) Filed: Jan. 9, 2003

(30) Foreign Application Priority Data

Nov. 29, 2002 (JP) ........................................ 2002-347356

(51) Int. Cl.[7] .................. C04B 22/00; C04B 22/08; C04B 22/10; C04B 22/16; A01N 59/20
(52) U.S. Cl. ................. 106/733; 106/15.05; 106/18.31; 106/18.32; 106/724; 106/727; 106/802; 106/808; 106/819; 106/823; 424/618
(58) Field of Search ................. 106/15.05, 18.31, 106/724, 727, 733, 802, 808, 819, 823; 424/618

(56) References Cited

U.S. PATENT DOCUMENTS 6,303,039 B1 * 10/2001 Back et al. ................. 210/764
6,509,057 B2 * 1/2003 Shigeru et al. ............... 427/11

FOREIGN PATENT DOCUMENTS

| JP | 6-247820 | * | 9/1994 |
| JP | 6-256052 | * | 9/1994 |
| JP | 6-298616 | * | 10/1994 |
| JP | 9-2849 | * | 1/1997 |
| JP | 10-218641 | * | 8/1998 |
| JP | 11-172154 | * | 6/1999 |
| JP | 2002-87858 | * | 3/2002 |
| JP | 2002-87861 | * | 3/2002 |
| JP | 2002-226242 | * | 8/2002 |

* cited by examiner

*Primary Examiner*—Anthony J. Green
(74) *Attorney, Agent, or Firm*—Oblon, Spivak, McClelland, Maier & Neustadt, P.C.

(57) ABSTRACT

The invention provides an antibacterial agent for concrete comprising a silver compound, a copper compound and an ion-retaining compound; a concrete composition comprising the antibacterial agent; and a concrete product produced from the concrete composition.

The concrete composition containing the antibacterial agent and the concrete product produced using the concrete composition show excellent antibacterial effect against causative bacteria of the corrosion of concrete such as sulfur reducing bacteria, sulfur oxidizing bacteria and carboxylic acid-producing bacteria, in particular, in sewage treatment plants.

26 Claims, No Drawings

ANTIBACTERIAL AGENT FOR CONCRETE, CONCRETE COMPOSITIONS AND CONCRETE PRODUCTS

FIELD OF THE INVENTION

The present invention relates to an antibacterial agent for concrete and more particularly to an antibacterial agent possessing an effect of controlling or inhibiting sulfur reducing bacteria and sulfur oxidizing bacteria, which are causative bacteria for the corrosion of concrete in, for instance, sewage treatment plants. Moreover, the present invention likewise relates to a concrete composition and a concrete product containing the foregoing antibacterial agent for concrete.

BACKGROUND ART

There has long been known that structures and duct lines made of concrete are corroded by the action of hydrogen sulfide and/or sulfuric acid generated by or in, for instance, sewage treatment plants. It has been confirmed that this concrete corrosion is caused by the action of sulfuric acid, which is formed from sulfuric acid salts present in sewage through sulfurous acid salts and/or elemental sulfur by the action of sulfur oxidizing bacteria belonging to, for instance, the genus Thiobacillus and/or sulfur reducing bacteria belonging to, for instance, the genus Desulfovibrio. The sulfuric add thus formed may convert concrete into fragile or brittle substances such as gypsum through a chemical reaction to thus reduce the strength of the concrete structures and/or duct lines at a stroke and to consequently damage the same. Up to this time, there have been employed techniques for preventing or dealing with the corrosion of this type such as the ventilation, the incorporation of a neutralizing agent into the same and surface treatment with a corrosion-resistant material, but they are not considered to be satisfactory measures from the viewpoint of the prevention of corrosion over a long period of time and maintenance.

Subsequently, there has been proposed a technique for solving the foregoing problems, which comprises the step of incorporating, into a concrete composition, an organic agent such as thiabendazole, nickel metal (see the following Patent 1) possessing an antibacterial action against the sulfur reducing bacteria, or antibacterial metal ion-caring inorganic powder (see the following Patent 2) to thus prevent any corrosion of concrete. In particular, the technique in which antibacterial metal ion-carryying inorganic powder is incorporated into concrete is an effective technique since such antibacterial metal ion-carrying inorganic powder has a growth-inhibitory effect not only on sulfur oxidizing bacteria, but also on sulfur reducing bacteria and carboxylic acid-producing bacteria. Incidentally, it is necessary to control the mixing ratio of cement, aggregates and water contained in a concrete composition to a desired range in order to impart a desired strength to a resulting concrete structure. For this reason, a new problem arises such that the antibacterial metal ion-carrying inorganic powder cannot be incorporated into a concrete composition in an amount sufficient for imparting a required bacterial growth-inhibitory effect to the concrete structure.

[Patent 1]: Japanese Un-Examined Patent Publication No. Hei 4-149053 (upper right column, line 12 to lower left column, line 4 on page 2);

[Patent 2]: Japanese Un-Examined Patent Publication No. Hei 9-60768 (right column, lines 7 to 47 on page 2).

SUMMARY OF THE INVENTION

A first object of the present invention is to provide an antibacterial agent for concrete having excellent antibacterial effect against causative bacteria for the corrosion of concrete such as sulfur reducing bacteria, sulfur oxidizing bacteria and carboxylic acid-producing bacteria present, in particular, in sewage treatment plants.

A second object of the present invention is to provide an antibacterial agent for concrete, which can impart, to a concrete composition having any mixing ratio, an excellent antibacterial effect on the causative bacteria of the corrosion of concrete.

A third object of the present invention is to provide a concrete composition, which comprises the aforementioned antibacterial agent for concrete.

A fourth object of the present invention is to provide a concrete product, which comprises the foregoing antibacterial agent for concrete.

A fifth object of the present invention is to provide a concrete product prepared using the foregoing antibacterial agent for concrete.

According to the present invention, there are provided an antibacterial agent for concrete, a concrete composition and a concrete product which are described below.

1. An antibacterial agent for concrete comprising a silver compound, a copper compound and an ion-retaining compound.
2. The antibacterial agent for concrete of the foregoing item 1 wherein the silver compound is at least one member selected from the group consisting of silver carbonate, silver oxide and silver phosphate.
3. The antibacterial agent for concrete of the foregoing item 1 or 2 wherein the copper compound is at least one member selected from the group consisting of copper carbonate, copper oxide, copper phosphate and copper hydroxide.
4. A concrete composition comprising an antibacterial agent for concrete as set forth in any one of the foregoing items 1 to 3.
5. A concrete product comprising an antibacterial agent for concrete as set forth in any one of the foregoing items 1 to 3.
6. A concrete product characterized in that it is produced using a concrete composition of the foregoing item 4.

BEST MODE FOR CARRYING OUT THE INVENTION

According to the present invention, there is provided an antibacterial agent for concrete, which comprises a silver compound, a copper compound and an ion-retaining compound.

In the present invention, an antibacterial agent for concrete can be prepared and the antibacterial agent permits the impartment of sufficient antibacterial properties to a concrete composition having any mixing ratio, if incorporating, into the antibacterial agent, a silver compound and a copper compound having high content of silver and copper respectively, as concrete corrosion-inhibitory components. Moreover, the incorporation of an ion-retaining compound into the agent of the present invention would permit the effective control of the liquation of the useful silver and copper components and the maintenance of the excellent antibacterial effect over a long period of time.

Therefore, the antibacterial agent for concrete according to the present invention inhibits the corrosion of concrete by the action of bacteria over a long period of time and thus permits the maintenance of the normal state of the concrete product.

The silver compounds used in the present invention are not restricted to specific ones inasmuch as they contain silver and these compounds are preferably those comprising a large quantity of silver, for instance, it is desirable to use those comprising silver in an amount of not less than 40% by mass, more preferably not less than 60% by mass and most preferably not less than 75% by mass. Examples of silver compounds preferably used in the present invention are silver carbonate (silver content: 78%), silver oxide (silver content: 93%), silver phosphate (silver content: 87%), silver chloride (silver content: 75%), silver fluoride (silver content: 85%), silver iodide (silver content: 46%), silver bromide (silver content: 57%), silver nitrate (silver content: 63%), silver sulfate (silver content: 69%), silver acetate (silver content: 65%), silver oxalate (silver content: 71%) and silver zeolite (for instance, those having a silver content of 5%). Among these examples, particularly preferred are silver carbonate, silver oxide and silver phosphate since these compounds are appropriately dissolved in sewage when they come in contact with the latter and they are liable to show their antibacterial effects therein. In this connection, a standard for the solubility of the compound in sewage when it comes in contact with the sewage is preferably set up at a level falling within the range of from 10 to 1000 ppm as expressed in terms of the solubility of silver in an artificial sewage.

The composition of such an artificial sewage is as follows: peptone: 67 mg/L; glucose: 67 mg/L; ammonium chloride: 156 mg/L; potassium primary phosphate: 12 mg/L; and potassium secondary phosphate: 12 mg/L.

The amount of the foregoing silver compound to be incorporated into the concrete composition desirably falls within the range of from 0.1 to 2.0% by mass, on the basis of the amount of the cement used, as expressed in terms of the amount of silver. This is because if the amount of the silver compound is less than the lower limit, antibacterial effect is insufficient, while if it exceeds the upper limit, any further improvement of the antibacterial effect is not expected and the use thereof in such an amount is uneconomical.

The copper compound used in the present invention is not restricted to any particular one inasmuch as it comprises copper, but preferably used herein are those having a high copper content such as those comprising copper in an amount of not less than 25% by mass, more preferably not less than 50% by mass and most preferably 60% by mass. Examples of preferred copper compounds are copper carbonate (copper content: 68%), copper oxide (copper content: 80%), copper phosphate (copper content: 50%), copper hydroxide (copper content: 65%), copper chloride (copper content: 47%), copper fluoride (copper content: 63%), copper iodide (copper content: 33%), copper bromide (copper content: 28%), copper nitrate (copper content: 34%), copper sulfate (copper content: 40%), copper acetate (copper content: 35%), copper oxalate (copper content: 42%) and copper zeolite (for instance, those having a copper content of 5%). Among these copper compounds, particularly preferred are copper carbonate, copper oxide, copper phosphate and copper hydroxide since these compounds are appropriately dissolved in sewage when they come in contact with the latter and they are liable to show their antibacterial effects therein. In this connection, a standard for the solubility of the compound in sewage when it comes in contact with the sewage is preferably set up at a level falling within the range of from 10 to 1000 ppm as expressed in terms of the solubility of copper in the artificial sewage.

The amount of the foregoing copper compound to be incorporated into a concrete composition desirably falls within the range of from 0.5 to 2.5% by mass on the basis of the amount of cement as expressed in terms of the amount of copper. This is because if the amount of the copper compound is less than the lower limit, antibacterial effect is insufficient, while if it exceeds the upper limit, any further improvement of the antibacterial effect is not expected and the use thereof in such an amount is uneconomical.

The ion-retaining compound used in the present invention means such a compound that it is linked with solubilized silver ions or copper ions to thus control the liquation of silver ions and copper ions. Examples of such ion-retaining compounds include oxides such as water-containing tin oxide, water-containing zirconium oxide and water-containing antimony oxide; hetero-polyacids such as molybdophosphoric acid salts and phosphotungstic acid salts; chelate compounds such as ethylenediaminetetraacetic acid salts and trinitrotriacetic acid salts; and phosphoric acid salts such a tripolyphosphoric acid salts and hexametaphosphoric acid salts.

The amount of the foregoing ion-retaining compound to be incorporated into a concrete composition desirably falls within the range of from 10 to 60% by mass on the basis of the amount of cement. This is because if the amount of the ion-retaining compound is less than the lower limit, the durability of the antibacterial effect in the concrete composition is insufficient, while if it exceeds the upper limit, any further improvement of the antibacterial effect is not expected and the use thereof in such an amount is uneconomical.

The particle size of the foregoing silver compound, copper compound and ion-retaining compound is not particularly limited, but these compounds are desirably in a finely pulverized condition, in particular, it is preferred that they are fine particles having an average particle size ranging from 0.001 to 0.1 mm, while taking into consideration the facts that these compounds, which are finely pulverized, can easily be admixed with, for instance, cement powder, fine aggregates and coarse aggregates and that they are liable to give a uniform mixture.

The relative ratio (by mass) of the silver compound, copper compound and ion-retaining compound present in the antibacterial agent for concrete according to the present invention is not particularly restricted inasmuch as the amounts of these compounds fall within the ranges specified above, respectively, but the ratio preferably ranges from 1:0.1:1 to 1:10:80 and more preferably 1:0.5:8 to 1:5:40.

The antibacterial agent of the present invention may directly be added to ingredients for concrete such as water, cement powder, fine aggregates and coarse aggregates, or further the antibacterial agent is preliminarily added to at least one member of ingredients of concrete such as water, cement powder, fine aggregates and coarse aggregates to form a concrete composition in advance and then the resulting composition is practically used.

The amount of the antibacterial agent for concrete according to the present invention to be incorporated into cement preferably ranges from 0.5 to 3.0% by mass and more preferably 0.8 to 1.5% by mass. If the amount of the antibacterial agent for concrete is less than the lower limit, antibacterial effect is insufficient, while if the amount thereof exceeds the upper limit, any further improvement of the antibacterial effect is not expected and the use thereof in such an amount is uneconomical.

The antibacterial agent for concrete according to the present invention can be added to concrete ingredients, concrete compositions and concrete products having any composition to thus impart antibacterial properties to these substances. Examples of such concrete products are manhole, Hume concrete pipes, Box Culvert, ready mixed concrete and mortar. In this respect, these concrete products may comprise other additive such as a water reducing agent, a fluidizing agent, a rust-proofing agent, a hardening-accelerating agent, a hardening-accelerator, a setting retarder, an inflating agent, fly ash and clinker.

These concrete products can be produced by any conventionally known method such as the centrifugal molding technique and the vibration molding technique.

In the concrete products to which the antibacterial agent of the present invention is applied, the concrete composition having any composition can be protected from any concrete corrosion by bacterial actions over a long period of time and the concrete products can maintain its normal conditions.

EXAMPLES

The present invention will hereunder be described in more detail with reference to the following Examples.

Examples 1 to 5 and Comparative Examples 1 to 3
(Preparation of Antibacterial Agent for Concrete and Production of Mortar Sample Bodies)

To a mortar component comprising 100 parts by mass of ordinary Portland cement, 200 parts by mass of sand and 50 parts by mass of water, there were added a silver compound, a copper compound and an ion-retaining compound specified in the following Table 1 in amounts likewise specified in Table 1, followed by sufficient mixing and stirring of these components in a mortar mixer and subsequent molding of the resulting mixture into a mortar sample having a size of 4×4×10 cm. As Comparative Examples, the procedures similar to those used above were repeated to form mortar samples free of any additive and comprising copper powder having an average particle size of 0.1 mm and thiabendazole. The mixing rate (as expressed in terms of parts by mass) of each sample will be summarized in the following Table 1.

Test Example 1 (Inspection of Mortar Samples for Bacterial Corrosion)

The resulting mortar samples were immersed in a culture medium (number of bacterial cells: $10^6$/ml) of a Thiobacillus strain (Thiobacillus thiooxidanse) at a temperature of 20±5° C. for 3 months. In this connection, the composition of the culture medium is shown in the following Table 2. Thereafter, each mortar sample was split by, for instance, a hammer and a 1% phenolphthalein solution was sprayed on the split surface thereof thus exposed for several seconds and the depth till the position at which the color of the phenolphthalein was changed to red after 10 minutes from the spray of phenolphthalein was determined and it was defined to be "corrosion depth (C.D.)". In this respect, the portion whose color was changed to red upon the phenolphthalein staining was the normal portion, while the remaining portions whose color was not changed to red were neutralized and weakened. The distance of the portion whose color was not changed to red in the direction of the depth, was determined using slide calipers at 5 positions per plane. The resulting average distance was subtracted from the size of the sample prior to the treatment and the half of the resulting value was defined to be the "corrosion depth (C.D.)". The results of the corrosion depths thus determined are listed in the following Table 3. The "corrosion depths" for all of the samples observed immediately before the initiation of the immersion were found to be 0 mm.

TABLE 1

Data used in the preparation of antibacterial agents for concrete and production of mortar samples

| Sample No. | Silver Compound | | Copper Compound | | Ion-retaining Comp. | |
| --- | --- | --- | --- | --- | --- | --- |
| | Kind | Amt.[1] | Kind | Amt.[1] | Kind | Amt.[1] |
| Ex. 1 | Silver carbonate | 0.3 (0.23 as Ag) | Copper hydroxide | 1.0 (0.65 as Cu) | Na EDTA | 10 |
| Ex. 2 | Silver oxide | 0.9 (0.84 as Ag) | Copper hydroxide | 2.2 (1.43 as Cu) | $H_2O$-containing tin oxide | 30 |
| Ex. 3 | Silver phosphate | 1.2 (1.04 as Ag) | Copper carbonate | 0.8 (0.54 as Cu) | Na EDTA | 10 |
| Ex. 4 | Silver phosphate | 2.0 (1.74 as Ag) | Copper phosphate | 2.0 (1.00 as Cu) | Silica | 60 |
| Ex. 5 | Silver zeolite | 2.0 (0.10 as Ag) | Copper oxide | 3.0 (2.40 as Cu) | Zeolite | 50 |
| Ex. 1* | Free of any antibacterial components. | | | | | |
| Ex. 2* | Containing 3.0 parts by mass of Ag powder as an antibacterial component. | | | | | |
| Ex. 3* | Containing 3.0 parts by mass of thiabendazole as an antibacterial component. | | | | | |
| Ex. 4* | Silver carbonate | 0.3 (0.23 as Ag) | None | — | Na EDTA | 10 |
| Ex. 5* | None | — | Copper carbonate | 0.8 (0.54 as Cu) | Na EDTA | 10 |

*Comparative Example
[1]Amount incorporated (the unit thereof is expressed in terms of "part by mass").

TABLE 2

Composition of the Culture Medium for Thiobacillus bacteria

| | |
| --- | --- |
| $(NH_4)_2SO_4$ | 2.0 g |
| $CaCl_2 \cdot 2H_2O$ | 0.3 g |
| $FeSO_2 \cdot 7H_2O$ | 0.01 g |
| $KH_2PO_4$ | 4.0 g |
| $MgSO_4 \cdot 7H_2O$ | 0.3 g |
| $Na_2S_2O_3 \cdot 5H_2O$ | 40.0 g |
| Bromophenol Blue | 0.002 g |
| Purified water | 1 L |

TABLE 3

Results of Microorganism-Corrosion Test for Mortar Samples

| Sample No. | Corrosion Depth (average value, mm) |
| --- | --- |
| Ex. 1 | 0.0 |
| Ex. 2 | 0.0 |
| Ex. 3 | 0.0 |
| Ex. 4 | 0.1 |
| Ex. 5 | 0.1 |
| Comp. Ex. 1 | 5.9 |
| Comp. Ex. 2 | 2.1 |
| Comp. Ex. 3 | 4.0 |
| Comp. Ex. 4 | 1.5 |
| Comp. Ex. 5 | 1.8 |

The data listed in Table 3 indicate that the mortar containing the antibacterial agent for concrete of the present invention shows a long lasting antibacterial effect as compared with the conventional antibacterial agents.

What is claimed is:

1. A concrete composition comprising:
   at least one silver compound,
   at least one copper compound and
   at least one ion-retaining compound, wherein the ion-retaining compound is selected from the group consisting of a water-containing tin oxide, water-containing zirconium oxide, water-containing antimony oxide, heteropolvacid(s), chelate compound(s), and phosphoric acid salt(s),
   cement,
   fine aggregates and/or coarse aggregates, and optionally, water.

2. The concrete composition of claim 1, wherein the silver content ranges from 0.1 to 2.0% by mass based on the amount of cement.

3. The concrete composition of claim 1, wherein the copper content ranges from 0.5 to 2.5% by mass based on the amount of cement.

4. The concrete composition of claim 1, wherein the ion-retaining compound ranges from 10 to 60% by massed based on the amount of cement.

5. The concrete composition of claim 1, wherein the particle size of the at least one silver compound, the at least one copper compound or the at least one ion-retaining compound, or two or more of said compounds, ranges from 0.001 to 0.1 mm.

6. The concrete composition of claim 1, wherein the ratio of the at least one silver compound to the at least one copper compound to the at least one ion-retaining compound ranges from 1:0.1:1 to 1:10:80.

7. The concrete composition of claim 1, wherein the ratio of the at least one silver compound, to the at least one copper compound to the at least one ion-retaining compound ranges from 1:0.5:8 to 1:5:40.

8. A concrete product comprising:
   at least one silver compound,
   at least one copper compound and
   at least one ion-retaining compound, wherein the ion-retaining compound is selected from the group consisting of a water-containing tin oxide, water-containing zirconium oxide, water-containing antimony oxide, heteropolyacid(s), chelate compound(s), and phosphoric acid salt(s),
   cement
   fine aggregates and/or coarse aggregates, and optionally, water.

9. The concrete product of claim 8, which is a molded concrete product.

10. The concrete product of claim 8, which is a manhole, Hume concrete pipe, box culvert or a concrete material used in sewage treatment.

11. The concrete product of claim 8, which is ready mixed concrete.

12. The concrete product of claim 8, which is mortar.

13. The concrete product of claim 8, wherein the combined amount of said silver, copper and ion-retaining compounds ranges form 0.5 to 3.0% by mass of the cement.

14. The concrete product of claim 8, further comprising one or more ingredients selected from the group consisting of a reducing agent, a fluidizing agent, a rust-proofing agent, a hardening agent, a hardening-accelerator agent, a setting retarder, and inflating agent, fly ash and clinker.

15. A method for making a concrete product, comprising:
   mixing at least one silver compound, at least one copper compound and at least one ion-retaining compound, wherein the ion-retaining compound is selected from the group consisting of a water-containing tin oxide, water-containing zirconium oxide, water-containing antimony oxide, heteropolyacid(s), chelate compound(s), and phosphoric acid salt(s) with water, cement powder, fine aggregates and coarse aggregates, and
   molding the mixture to produce a concrete product.

16. A method for inhibiting the growth of sulfur-oxidizing bacteria comprising:
   incorporating into a concrete product at least one silver compound, at least one copper compound and at least one ion-retaining compound,
   wherein the ion-retaining compound is selected from the group consisting of a water-containing tin oxide, water-containing zirconium oxide, water-containing antimony oxide, heteropolvacid(s), chelate compound(s), and phosphoric acid salt(s)
   in an amount sufficient to inhibit the growth of said sulfur-oxidizing bacteria.

17. A method for inhibiting the growth of sulfur-reducing bacteria comprising:
   incorporating into a concrete product at least one silver compound, at least one copper compound and at least one ion-retaining compound, wherein the ion-retaining compound is selected from the group consisting of a water-containing tin oxide, water-containing zirconium oxide, water-containing antimony oxide, heteropolyacid(s), chelate compound(s), and phosphoric acid salt(s)
   in an amount sufficient to inhibit the growth of said sulfur-reducing bacteria.

18. A method for inhibiting the growth of carboxylic acid-producing bacteria comprising:
   incorporating into a concrete product at least one silver compound, at least one copper compound and at least one ion-retaining compound, wherein the ion-retaining compound is selected from the group consisting of a water-containing tin oxide, water-containing zirconium oxide, water-containing antimony oxide, heteropolyacid(s), chelate compound(s), and phosphoric acid salt(s)
   in an amount sufficient to inhibit the growth of said carboxylic acid-producing bacteria.

19. The concrete composition of claim 1, wherein the silver compound comprises silver carbonate.

20. The concrete composition of claim 1, wherein the silver compound comprises silver oxide.

21. The concrete composition of claim 1, wherein the silver compound comprises silver phosphate.

22. The concrete composition of claim 1, wherein the copper compound comprises copper carbonate.

23. The concrete composition of claim 1, wherein the copper compound comprises copper phosphate.

24. The concrete composition of claim 1, wherein the copper compound comprises copper hydroxide.

25. The concrete composition of claim 1, wherein the at least one silver compound is selected from the group consisting of silver carbonate, silver oxide and silver phosphate, and the at least one copper compound is selected from the group consisting of copper carbonate, copper oxide, copper phosphate and copper hydroxide.

26. The concrete composition of claim 1, wherein the at least one ion-retaining compound is selected from the group consisting of molybdophosphoric acid salt(s), phosphotungstic acid salt(s), ethylenediaminetetraacetic acid salt(s), trinitrotriacetic acid salt(s), tripolyphosphoric acid salt(s) and hexametaphosphoric acid salt(s).

* * * * *